United States Patent [19]

Hill

[11] Patent Number: 5,244,459
[45] Date of Patent: Sep. 14, 1993

[54] SUCTION IRRIGATOR ENDOSCOPE

[76] Inventor: Raymond R. Hill, 5100 Apache Dr., Stage Coach, Nev. 89429

[21] Appl. No.: 826,972

[22] Filed: Jan. 28, 1992

[51] Int. Cl.$^5$ ............................................. A61M 5/00
[52] U.S. Cl. ...................................... 604/33; 604/249
[58] Field of Search .......................... 604/27, 30–34, 604/119, 164, 169, 246, 248, 249, 256; 128/4, 6

[56] References Cited

U.S. PATENT DOCUMENTS

| | | | |
|---|---|---|---|
| 1,740,174 | 12/1929 | Hevern | 604/248 |
| 3,081,770 | 3/1963 | Hunter | 604/33 |
| 3,678,959 | 7/1972 | Liposky | 604/249 |
| 3,791,379 | 2/1974 | Storz | 128/4 |
| 4,680,026 | 7/1987 | Weightman et al. | 604/33 |
| 4,769,018 | 9/1988 | Wilson | 604/248 |
| 4,881,523 | 11/1989 | Heckele | 128/4 |
| 5,125,910 | 6/1992 | Freitas | 604/249 |
| 5,186,714 | 2/1993 | Boudreault et al. | 604/33 |
| 5,188,591 | 2/1993 | Dorsey, III | 604/33 |

Primary Examiner—John D. Yasko
Assistant Examiner—Anthony Gutowski
Attorney, Agent, or Firm—Kelly Bauersfeld & Lowry

[57] ABSTRACT

A surgical endoscope includes an elongated cannula having a distal end for insertion into the body of a patient, and a proximal end having a valve assembly mounted thereon to selectively and alternatively connect the cannula to a source of irrigation fluid, or to an aspirator. The valve assembly includes a pair of valve members adapted for manual operation one at a time to permit irrigation or suction fluid flow to a central flow chamber disposed at the proximal end of the cannula. The valve members are symmetrically mounted at opposite sides of the central flow chamber for movement between opened and closed positions without occluding the proximal end of the cannula. An instrument access port on the valve assembly at a position in-line with the cannula permits introduction of a surgical instrument through the central flow chamber and cannula, independently of the valve members and manipulation thereof.

11 Claims, 3 Drawing Sheets

SUCTION IRRIGATOR ENDOSCOPE

BACKGROUND OF THE INVENTION

This invention relates generally to improvements in suction irrigator devices for use in endoscopic surgery. More particularly, this invention relates to an improved surgical endoscope designed for selectively irrigating or aspirating a surgical site, in combination with facilitating introduction of a surgical instrument to the site.

Endoscopic surgery is generally known in the art wherein surgical procedures are performed on a patient by manipulating one or more surgical instruments introduced to a surgical site through an elongated hollow tube. More particularly, one or more hollow tubes or endoscopes are passed through relatively small incisions to position distal ends thereof at selected positions within the body of a patient for purposes of performing a surgical procedure. Small surgical instruments are then passed through the tubes to access the surgical site and to perform the surgical procedure with minimal disruption and associated trauma to patient tissues. Typically, at least one of the surgical instruments comprises an optical fiber probe to illuminate the surgical site and permit viewing thereof on a television screen or monitor. A variety of additional small surgical instruments such as laser probes, cautery hooks, biopsy forceps, clamps, and the like have been adapted for use in endoscopic surgical procedures.

In performing endoscopic surgery, it is frequently necessary to deliver a fluid to the surgical site. For example, it is known to deliver a gas through an endoscopic tube for purposes of inflating a patient cavity and thereby facilitate subsequent introduction and manipulation of surgical instruments. Similarly, it is known to deliver an irrigation fluid to the surgical site, and/or to connect the endoscopic tube to a suction system for purposes of aspirating fluid from the patient. In a typical endoscopic surgical procedure, the need for fluid irrigation and aspiration can occur at different times.

In the past, surgical endoscopes have been developed to include means for irrigating or aspirating a surgical site via an endoscopic tube which may also be used for introducing a surgical instrument. In general, however, such suction irrigator endoscopes have included small valve members adapted for manual manipulation to connect the endoscope to an irrigation fluid source or to a hospital suction unit. The small valve members have been relatively difficult to manipulate, particularly by a surgeon or surgical staff member having large hands and fingers. Moreover, the valve members have been designed typically in a manner permitting simultaneous connection of the endoscope to an irrigation fluid and to the suction unit. Alternative endoscope designs aimed at preventing simultaneous suction/irrigation operation have undesirably been limited to use with flexible surgical instruments such as optical fiber cables and the like.

The present invention provides an improved suction irrigator endoscope designed for connecting an elongated endoscopic tube or cannula to an irrigation fluid, or alternately to an aspirator. The improved endoscope of the present invention positively precludes simultaneous connection of the cannula to the irrigation fluid source and aspirator, while permitting substantially unobstructed introduction through the cannula of any one of a wide range of available surgical instruments.

SUMMARY OF THE INVENTION

In accordance with the invention, an improved suction irrigator endoscope is provided for use in endoscopic surgery to permit selective irrigation or aspiration of a surgical site within the body of a patient, in combination with substantially unobstructed and unrestricted introduction of an endoscopic surgical instrument to the surgical site.

In a preferred form, the improved endoscope comprises an elongated and typically rigid endoscopic tube or cannula having a distal end adapted for insertion through a small incision into the body of a patient, and a proximal end disposed outside the patient's body and having a valve assembly mounted thereon. The valve assembly comprises a valve housing having a central flow chamber in open communication with the proximal end of the cannula. The central flow chamber communicates in turn with a pair of flow ports adapted for connection respectively to a source of irrigation fluid, and to a suction unit.

The valve assembly further includes a pair of movable valve members which are spring-loaded for normally closing the irrigation and suction flow ports, thereby preventing irrigation fluid flow to and suction fluid flow from the central flow chamber. The valve members are symmetrically mounted at opposite ends of the valve assembly, in association with a shuttle actuator mounted for back-and-forth sliding movement on the valve housing. The shuttle actuator is normally retained by the spring-loaded valve members in a centered position with both flow ports closed. The shuttle actuator is movable in either direction to displace one but not both of the valve members for purposes of opening the flow port associated with the displaced valve member. The nondisplaced valve member is retained by the shuttle actuator in the closed position, thereby preventing simultaneous opening of both flow ports.

An instrument access port on an aft end of the valve housing is disposed substantially in-line with the cannula and the central flow chamber. An endoscopic surgical instrument of rigid or flexible construction may be passed through the access port and further through the central flow chamber and cannula for introduction to and use at the surgical site. Introduction and/or withdrawal of the surgical instrument is unaffected by the opened or closed position of the valve members.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
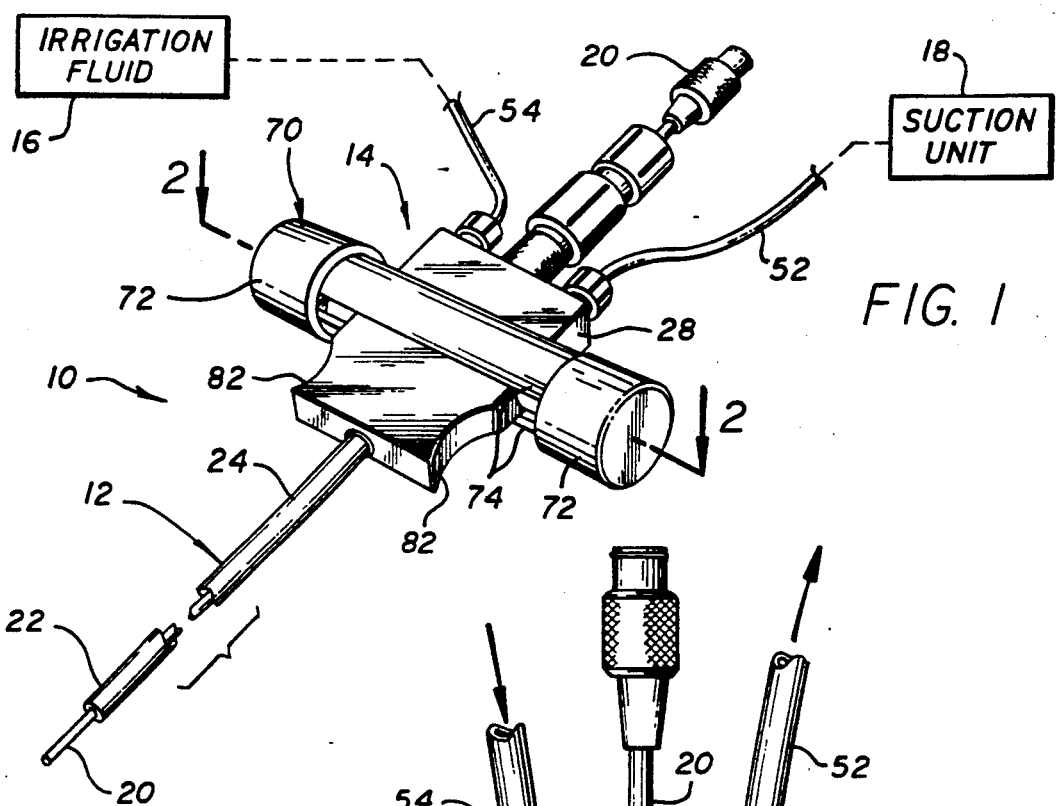
FIG. 1 is a perspective view illustrating an improved suction irrigator endoscope embodying the novel features of the invention.

As shown in the exemplary drawings, an improved suction irrigator endoscope referred to generally in FIG. 1 by the reference numeral 10 is provided for use in endoscopic surgery. The improved endoscope 10 includes an elongated endoscopic tube or cannula 12 adapted for insertion into the body of a patient, in combination with a valve assembly 14 which can be manipulated in a selective manner to connect the cannula 12 to an irrigation fluid source 16, or alternately to a suction unit 18. In addition, the valve assembly 14 is designed to permit substantially unobstructed insertion of an elongated endoscopic surgical instrument 20 for performing a selected surgical procedure within the body of the patient.

The suction irrigator endoscope 10 of the present invention is designed for use in a wide variety of endoscopic surgical procedures wherein the cannula 12 provides access to a selected surgical site within the body of a patient. More particularly, as generally known in the art, one or more endoscopes are typically passed through small incisions to position distal ends thereof in proximity to a selected site for performance of a surgical procedure. An optical fiber cable commonly comprises one surgical instrument passed through one of the endoscopes and operable to illuminate the surgical site for viewing on a television screen or monitor. One or more additional endoscopes accommodate passage of other surgical instruments such as laser probes, biopsy forceps, clamps, cautery hooks, and the like used to perform the desired surgical procedure. Beneficially, the surgical instruments are physically manipulated from a position outside the patient, and all of the instruments and associated endoscopes are withdrawn through the associated small incisions at the conclusion of the surgery, resulting in minimizing the overall trauma to patient tissue. The suction irrigator endoscope 10 of the present invention accommodates removable passage of one of the surgical instruments in a endoscopic procedure, while additionally provided selective operation to irrigate or aspirate the surgical site, as described.

Figure 2:
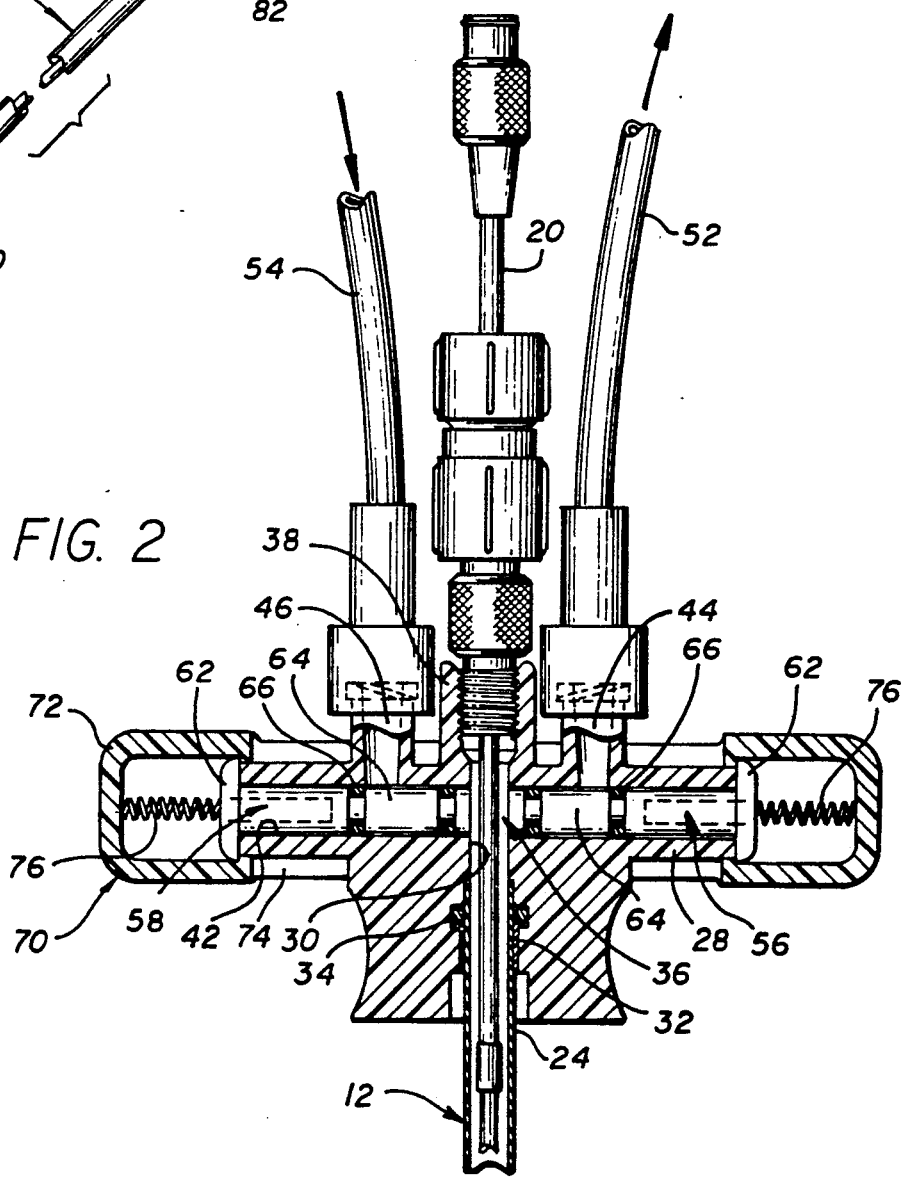
FIG. 2 is an enlarged fragmented horizontal sectional view taken generally on the line 2—2 of FIG. 1.

In general terms, as shown in FIGS. 1 and 2, the improved endoscope 10 comprises the elongated endoscopic tube or cannula 12 which, in a preferred form, has a rigid hollow tubular construction formed from surgical grade stainless steel or the like. The cannula 12 is designed to fit through a small incision in the patient's skin to permit positioning of a distal end 22 in selected orientation with a target surgical site. A proximal end 24 of the cannula carries the valve assembly 14 designed to accommodate selective connection with the irrigation fluid 16, or with the suction unit 18, while simultaneously accommodating removable introduction and/or withdrawal of the selected surgical instrument 20 with respect to the surgical site. In this regard, with the surgical instrument 20 installed within the cannula 12, sufficient radial clearance is present between the instrument and cannula to permit irrigation or suction fluid flow.

The valve assembly 14 comprises, in a preferred form, a unitarily formed valve housing 28 which can be provided as a lightweight and inexpensive plastic molding. The valve housing 28 includes a forward or nose end having a central bore 30 (FIGS. 2-4) formed therein and adapted to receive the proximal end 24 of the cannula 12. A sealing sleeve 32 and associated O-ring seal 34 may be provided to insure a secure sealed connection, if desired. The central bore 30 extends substantially linearly and in a substantially uninterrupted manner through a central flow chamber 36 to an instrument access port 38 defined by a threaded fitting at an aft end of the valve housing 28. The surgical instrument 20, such as a laser probe or any other type of standard endoscopic instrument, can be introduced via the access port 38 for passage through the housing bore 30 and the cannula 12 to the surgical site.

The central flow chamber 36 within the valve housing 28 is defined by the intersection of a transverse cross-bore 42 with the central bore 30. In this regard, the housing 28 protrudes outwardly in laterally opposite directions from the central flow chamber 36, with the cross bore 42 communicating with a pair of flow ports 44 and 46 defined by luer type fittings on the aft end of the valve housing 28. These luer fittings are positioned substantially in transverse in-line relation with the instrument access port and fitting 38. The luer fittings associated with the flow ports 44 and 46 are adapted for respective connection through tubing 52 and 54 to the suction unit 18 and to the irrigation fluid source 16. In this regard, the irrigation fluid source may comprise a source of pressurized gas for controlled inflation of a patient body cavity, or otherwise comprise a source of irrigation fluid such as sterile saline or the like for flooding a surgical site. The suction unit 18 typically comprises an aspiration system of the type commonly available in a medical operating room environment.

The cross-bore 42 formed in the valve housing 28 opens outwardly in opposite directions, as viewed best in FIG. 2. A pair of valve members 56 and 58 include cylindrical stems received in a sliding manner within the cross bore 42, with the cylindrical stems being joined at their outboard ends to radially enlarged heads 62. The head 62 of each valve member 56, 58 is sized to overlie the outboard face of the valve housing 28 at the associated outboard end of the cross-bore. When the head 62 engages the outboard face of the valve housing, an inner spool 64 on the valve stem generally overlies and closes the associated flow port 44, 46, without projecting into the central flow chamber 36, or otherwise interfering with surgical instrument passage through the flow chamber 36. An axially spaced pair of O-ring seals 66 on the spool 64 positively prevent fluid passage through the associated flow port.

A shuttle actuator 70 is mounted on the exterior of the valve housing 28 for controllably operating the valve members 56 and 58. As shown best in FIGS. 1 and 2, the shuttle actuator comprises a pair of closed-ended cylindrical end caps 72 interconnected by a pair of slide legs 74. The slide legs 74 are spaced apart from one another to receive the valve housing 28 therebetween, while permitting back-and-forth sliding motion of the shuttle actuator 70 thereon. A pair of compression springs 76 are seated within counterbores formed in the valve members 56, 58, and react compressibly against the inboard faces of the end caps 72 for normally maintaining the shuttle actuator 70 in a centered position (FIG. 1 and 2) with both valve members 56, 58 maintained in a closed condition relative to the flow ports 44, 46.

Figure 3:
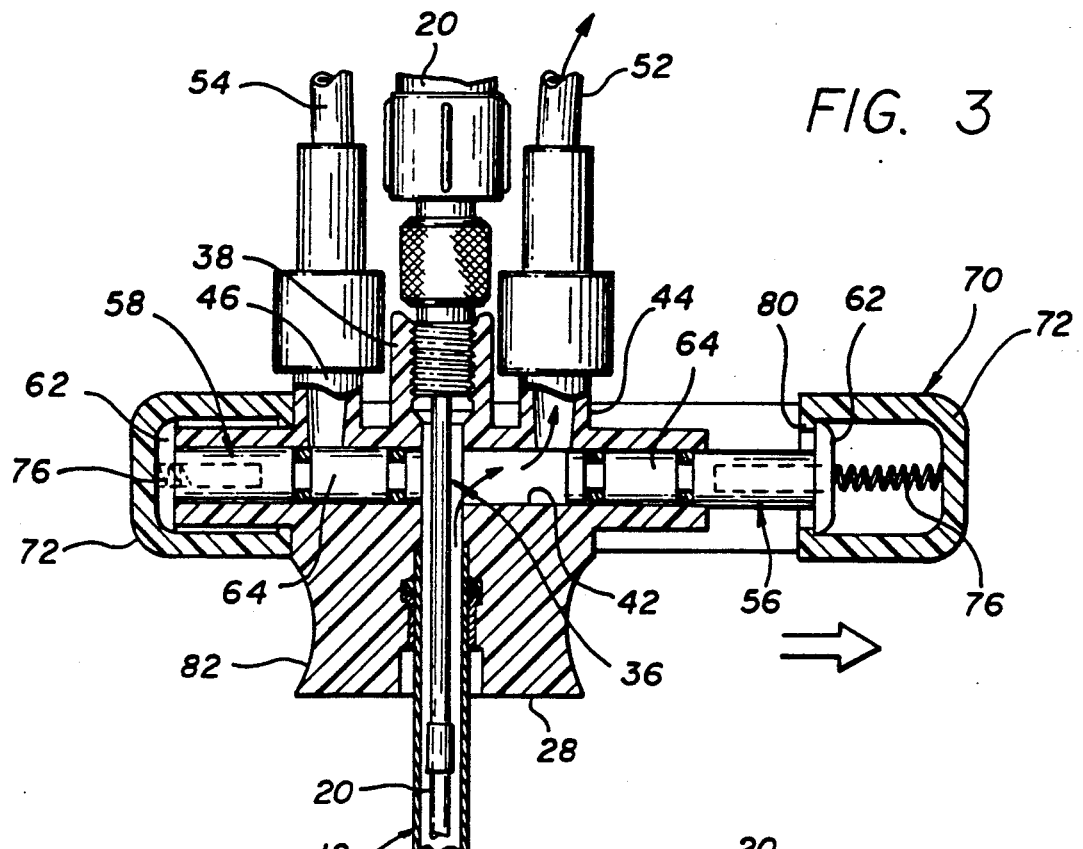
FIG. 3 is an enlarged sectional view similar to FIG. 2, but illustrating a valve assembly manipulated to permit suction fluid flow.

Shifting movement of the shuttle actuator 70 to the right as viewed in FIG. 3 causes an internal rib 80 on the right-hand end cap 72 to engage a peripheral edge of the valve head 62 on the right-hand valve member 56. Such engagement retracts the valve member 56 within the cross-bore 42 sufficiently to open the suction flow port 44 to the central flow chamber 36. In this configuration, the suction unit 18 is coupled in flow communication with the interior of the cannula 12 for aspirating fluid from the surgical site. Importantly, during such fluid aspiration step, the left hand end cap 72 compresses the centering spring 76 associated therewith and physically retains the left-hand valve member 58 in the closed position.

Figure 4:
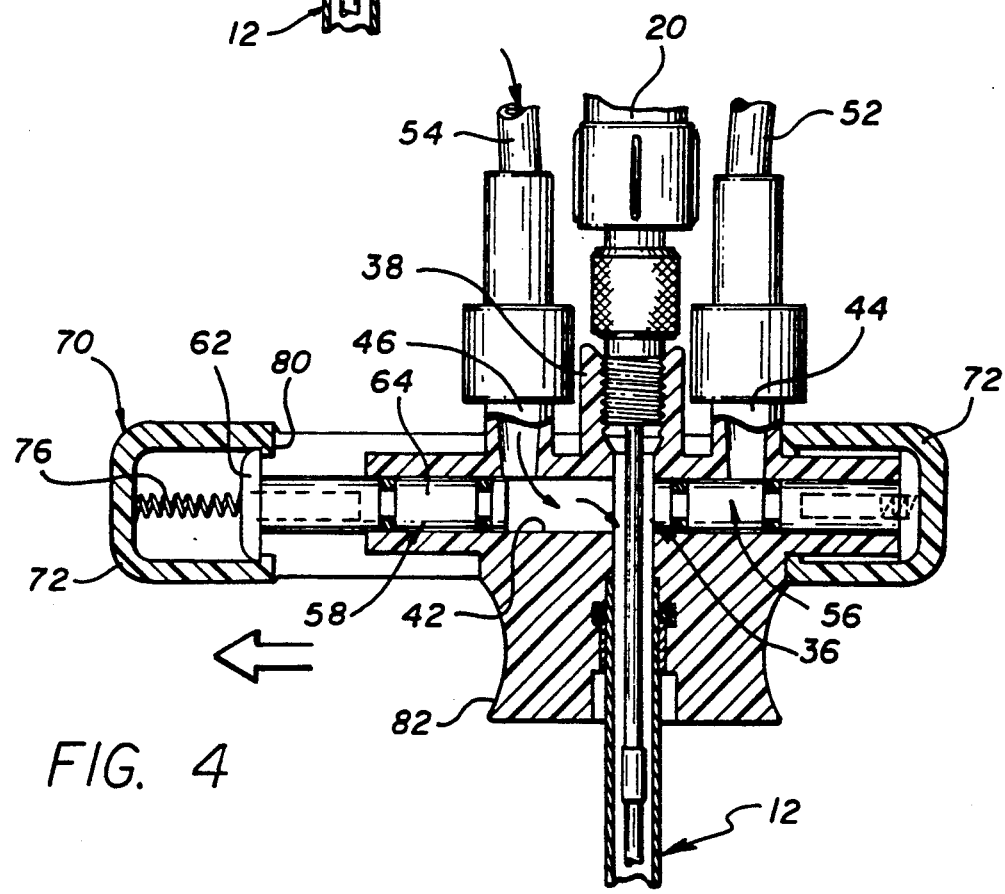
FIG. 4 is an enlarged fragmented sectional view similar to FIGS. 2 and 3, but depicting valve assembly manipulation to permit irrigation fluid flow.

Conversely, shifting movement of the shuttle actuator 70 to the left as viewed in FIG. 4 achieves opposite manipulation of the valve members 56, 58. More particularly, the right-hand end cap 72 functions to retain the right-hand valve member 56 in the closed position, whereas the internal rib 80 on the left-hand end cap 72 retracts the left-hand valve member 58 and thereby opens the irrigation flow port 46 to the irrigation fluid source 16 with the cannula 12. In either case, regardless of the direction in which the shuttle actuator 70 is shifted, simple release of the shuttle actuator results in spring-loaded return to the centered position with both valve members closed. Moreover, regardless of the position of the shuttle actuator 70 and the associated valve members 56, 58, the central flow chamber 36 is unobstructed at all times to permit insertion and withdrawal of various surgical instruments as may be required throughout the course of a surgical procedure.

The valve members 56 and 58, and the associated shuttle actuator 70, are mounted symmetrically on the valve housing 28, on opposite sides of the central flow chamber 36. This symmetric geometry provides a balanced instrument which can be manipulated quickly and easily by the surgeon or a member of a surgical team to provide the desired suction or irrigation function. The endoscope conveniently includes recessed finger grips 82 formed symmetrically at the forward or nose end of the valve housing, thereby providing facilitated fingertip manipulation by left-handed or right-handed persons, and substantially at any orientation of the endoscope. If necessary or desirable, appropriate coding such as color codes or the like may be applied to the luer fittings associated with the suction and irrigator flow ports 44, 46 to prevent undesired cross-connection with the irrigation fluid and suction unit. At the end of a surgical procedure, the entire endoscope is withdrawn from the patient along with any surgical instrument installed therein. The endoscope 10 may be conveniently and economically discarded after use.

Figure 5:
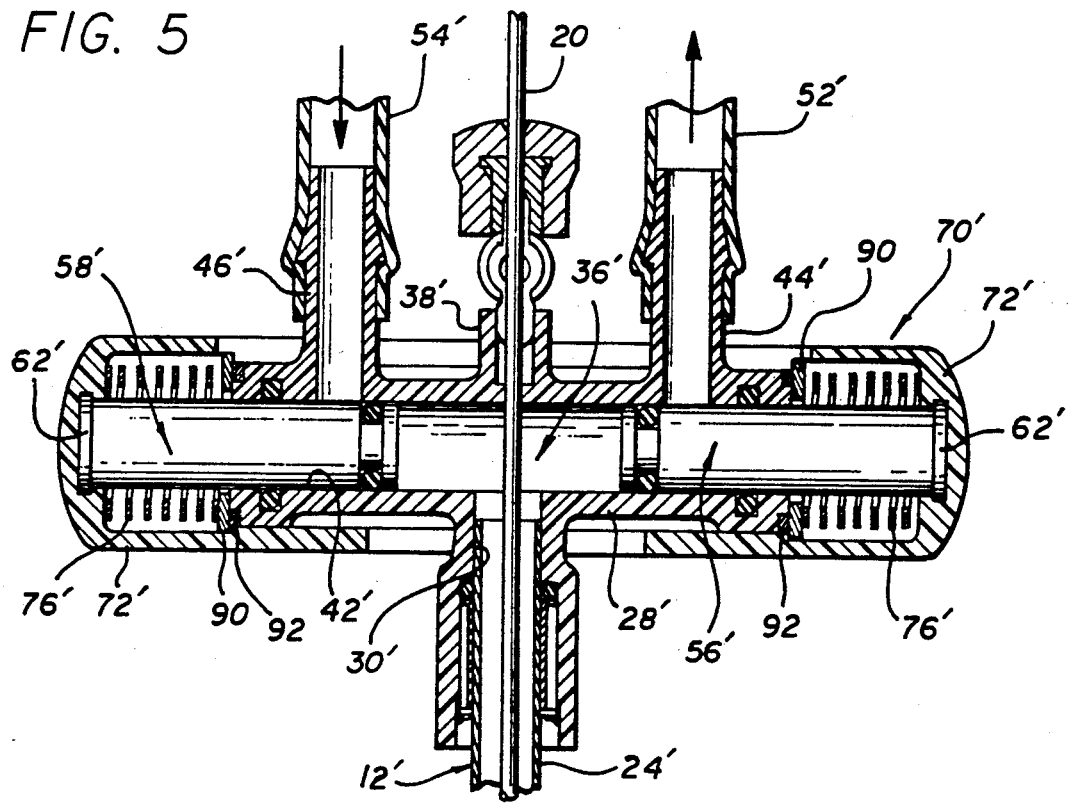
FIG. 5 is an enlarged fragmented horizontal sectional view similar to FIG. 2, and depicting one alternative preferred form of the invention.
Figure 6:
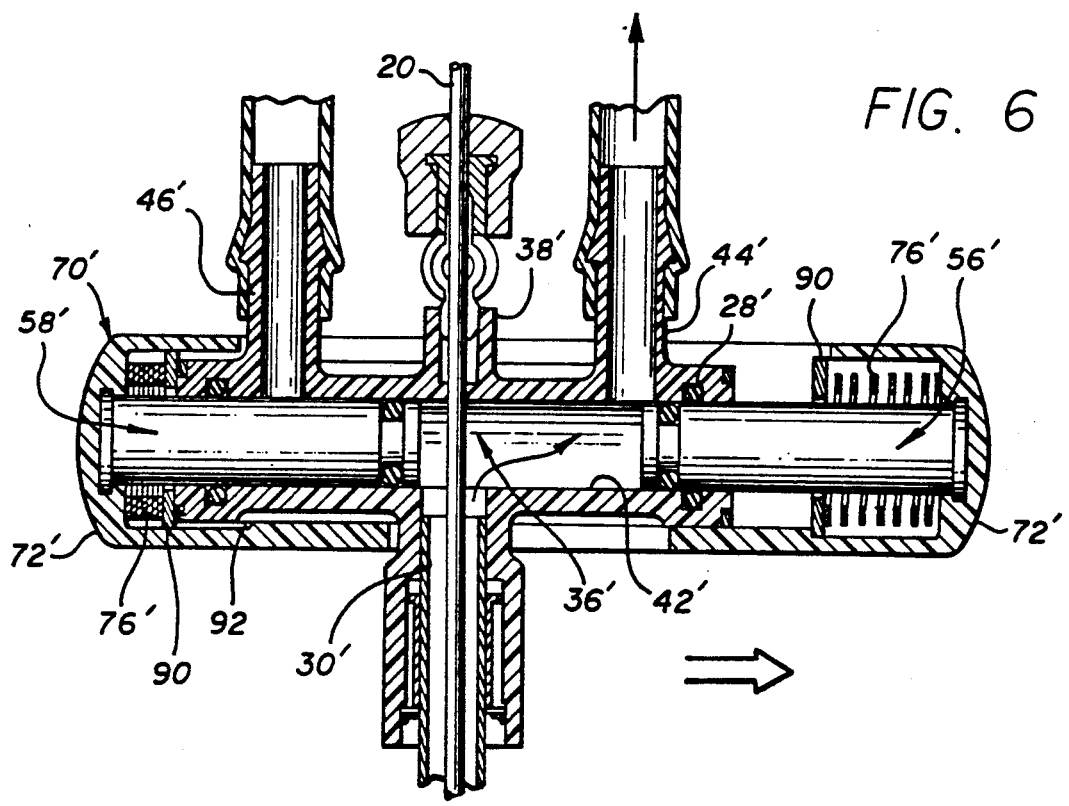
FIG. 6 is an enlarged sectional view similar to FIG. 5, and depicting a valve assembly shifted to a position permitting suction fluid flow.

An alternative preferred form of the invention is shown in FIGS. 5 and 6, wherein components corresponding in structure and function to those previously described are identified by common primed reference numerals. In this embodiment, a valve housing 28' again includes a nose end for sealed mounting onto the proximal end 24' of a cannula 12'. A central bore 30, within the valve housing 28' extends substantially in-line or linearly to an access port 38' at an aft end of the housing. A selected surgical instrument 20 can be introduced through the access port 38' and the bore 30' for passage through the hollow cannula 12' to the surgical site.

A cross-bore 42' in the valve housing 28' intersects the central bore 30, to define a central flow chamber 36'. Suction and irrigation flow ports 44' and 46' open into the cross-bore at opposite sides of the central flow chamber 36', with the flow ports 44', 46' and access port 38' being arranged in-line. The flow ports 44', 46' are shown in association with barbed fittings for press-in connection to tubing 52' and 54' coupled to a suction unit and to an irrigation fluid source, as previously described. A pair of valve members 56' and 58' have cylindrical stems projecting into the opposite ends of the cross-bore 42' to open or close the respective flow ports 44', 46'. These valve members 56', 58' have enlarged heads 62' for snug-fit mounting into mating recesses formed at the inboard faces of a pair of end caps 72' on a shuttle actuator 70'. As in the previous embodiment, the shuttle actuator 70' is mounted on the valve housing 28' for back-and-forth sliding motion to open one of the suction and irrigation flow ports 44', 46'.

The shuttle actuator 70' is springably retained in a normally centered position as viewed in FIG. 5 with both valve members 56', 58' in closed positions. More particularly, a compression spring 76' reacts between an inboard face of each end cap 72' and a retainer ring 90 seated against a shoulder 92 on the shuttle actuator. In the normal centered position of FIG. 5, both of the centering springs 76' are slightly compressed such that the associated retainer rings 90 transfer opposing spring forces to the opposite end faces of the valve housing 28'. However, manual displacement of the shuttle actuator 70' in either direction retracts one of the valve members 50', 58 to an open position, while simultaneously advancing the other valve member within the cross-bore 42' to a still-closed position without projecting into the central flow chamber 36'. The movement is shown in FIG. 6 for purposes of opening the suction flow port 44' to the central flow chamber 36'. In this position the suction valve member 56' is retracted to the open position, and the spring 76' associated with the irrigation valve member 58' is compressed for spring-loaded return of the shuttle actuator to the centered position when released.

A variety of further modifications and improvements to the suction irrigation endoscope of the present invention will be apparent to those skilled in the art. Accordingly, no limitation on the invention is intended by way of the foregoing description and accompanying drawings, except as set forth in the appended claims.

What is claimed is:

1. A suction irrigator endoscope, comprising:
    an elongated cannula having a distal end adapted for surgical insertion into the body of a patient;
    a valve housing mounted on a proximal end of said cannula and defining a central flow chamber in flow communication with said cannula, a suction flow port adapted for communication to a suction source, and an irrigation fluid flow port adapted for connection to an irrigation fluid source; and
    valve means movable with respect to said flow ports for connecting said flow ports one at a time in flow communication with said central flow chamber;
    said valve means being movable to a first position disconnecting both of said flow ports from said central flow chamber, a second position connecting said suction flow port to said central flow chamber, and a third position connecting said irrigation fluid flow port to said central flow chamber, said valve means being disposed outside said central flow chamber in each of said first, second and third positions, and said valve means further including spring means for normally biasing said valve means to said first position;

said valve means further including means for positively maintaining said irrigation fluid flow port disconnected from said central flow chamber when said valve means is in said second position and for positively maintaining said suction fluid port disconnected said central flow chamber when said valve means is in said third position;

said valve housing further defining an instrument access port disposed substantially in-line with said central flow chamber and said cannula to permit introduction of an endoscopic instrument through said access port and said central flow chamber and further through said cannula substantially to said distal end thereof.

2. The suction irrigator endoscope of claim 1 wherein said flow ports and said access port are disposed substantially in-line with each other, said flow ports being disposed on opposite sides of said access port.

3. A suction irrigator endoscope, comprising:
an elongated cannula having a distal end adapted for surgical insertion into the body of a patient;
a valve housing mounted on a proximal end of said cannula and defining a central flow chamber in flow communication with said cannula, a suction flow port adapted for connection to a suction source, and an irrigation fluid flow port adapted for connection to an irrigation flood source; and
valve means movable with respect to said flow ports for connecting said flow ports one at a time in flow communication with said central flow chamber, said valve means being positioned outside said central flow chamber;
said valve means including passage means communication with flow ports with said central flow chamber, a pair of valve members movably mounted within said passage means in respective association with said flow ports, said valve members being movable between opened and closed positions to respectively connect and disconnect their associated flow ports with said central flow chamber;
said valve means further including a shuttle actuator mounted slidably upon said valve housing, and spring means reacting between said shuttle actuator and each of said valve members for normally retaining both of said valve members in a closed position;
said shuttle actuator being slidably movable in one direction relative to said valve housing to displace one of said valve members to the open position, said shuttle actuator being slidably movable in an opposite direction relative to said valve housing to displace the other of said valve members to the open position;
said valve housing further defining an instrument access port disposed substantially in-line with said central flow chamber and said cannula to permit introduction of an endoscopic instrument through said access port and said central flow chamber and further through said cannula substantially to said distal end thereof.

4. The suction irrigator endoscope of claim 3 wherein said shuttle actuator positively retains said other valve member in the closed position upon movement of said shuttle actuator in said one direction, and positively retains said one valve member in the closed position upon movement of said shuttle actuator in said other direction.

5. The suction irrigator endoscope, comprisng:
an elongated cannula having a distal end adapted for surgical insertion into the body of a patient;
a vale housing mounted on a proximal end of said cannula and defining a central bore disposed substantially in-line with and in flow communication with said cannula, an instrument access port at an end of said central bore opposite said cannula, a cross-bore intersecting said central bore and cooperating at the intersection to define a central flow chamber, a suction flow port communicating with said cross-bore on one side of said central flow chamber, and an irrigation fluid flow port communicating with said cross-bore on an opposite side of said central flow chamber;
a pair of valve members slidably received into said cross-bore on opposite sides of the central flow chamber, each of said valve members being movable between opened and closed positions for respectively connecting and disconnecting the flow port associated therewith in flow communication with said central flow chamber, substantially without movement of said valve members into said central flow chamber;
a shuttle actuator mounted slidably on said valve housing for back-and-forth movement in a direction generally coinciding with a longitudinal axis of said cross-bore;
spring means reacting between said shuttle actuator and said valve members for urging said shuttle actuator to a first, substantially centered position on said valve housing, and for urging both of said valve members to a closed position; and
connector means engageable with said shuttle actuator upon sliding movement on said valve housing in one direction from said first position for displacing one of said valve members to the open position, and for displacing the other of said valve members to the open position upon sliding movement on said valve housing in an opposite direction from said first position;
said access port permitting introduction an endoscopic instrument through said access port and said central flow chamber and further through said cannula substantially to said distal end thereof.

6. The suction irrigator endoscope of claim 5 further including means for normally positioning both of said valve members in the closed position.

7. The suction irrigator endoscope of claim 5 wherein said cross-bore opens at opposite ends to the exterior of said valve housing, said valve members being slidably receivable into the opposite ends of said cross-bore.

8. The suction irrigator endoscope of claim 7 wherein said valve members are slidably movable together with said shuttle actuator.

9. The suction irrigator endoscope of claim 7 wherein said valve members are independently movable with said shuttle actuator upon movement of said shuttle actuator in opposite direction from said first position.

10. A suction irrigator endoscope, comprising:
an elongated cannula having a distal end adapted for surgical insertion into the body of a patient;
a valve housing mounted on a proximal end of said cannula and defining a central flow chamber in flow communication with said cannula, a suction flow port adapted for connection to a suction source, and an irrigation fluid flow port adapted for connection to an irrigation fluid source; and valve means movable with respect to said flow ports for connecting said flow ports one at a time in flow communication with said central flow chamber, said valve means being movable to a first position disconnecting both of said flow ports from said central flow chamber, a second position connecting said suction flow port to said central flow chamber, and a third position connecting said irrigation fluid flow port to said central flow chamber, said valve means being disposed outside said central flow chamber in each of said first, second and third positions, and said valve means further including spring means for normally biasing said valve means to said first position;

said valve means including passage means communicating said flow ports with said central flow chamber, a pair of valve members movably mounted within said passage means in respective association with said flow ports, said valve members being movable between opened and closed positions to respectively connect and disconnect their associate flow ports with said central flow chamber, said valve means further including a shuttle actuator mounted slidably upon said valve housing for movement in one direction to displace one of said valve members to the open position and in an opposite direction to displace the other of said valve members to the open positions, said spring means reacting between said shuttle actuator and each of said valve members for normally retaining both of said valve members in a closed position.

11. The suction irrigator endoscope of claim 10 wherein said shuttle actuator positively retain said other valve member in the closed position upon movement of said shuttle actuator in said one direction, and positively retains said one valve member in the closed position upon movement of said shuttle actuator in said other direction.

* * * * *